United States Patent [19]

Makisumi et al.

[11] Patent Number: 4,535,088

[45] Date of Patent: Aug. 13, 1985

[54] PROPYNYLAMINOTHIAZOLE DERIVATIVES

[75] Inventors: Yasuo Makisumi, Hyogo; Akira Murabayashi; Katsuya Tawara, both of Osaka; Yoshihachi Watanabe, Shiga; Toshio Takahashi, Hyogo, all of Japan

[73] Assignee: Shionogi & Co., Ltd., Osaka, Japan

[21] Appl. No.: 557,365

[22] Filed: Dec. 2, 1983

[30] Foreign Application Priority Data

Dec. 21, 1982 [JP] Japan .................................. 57-225271

[51] Int. Cl.$^3$ ..................... C07D 277/42; A01N 43/78
[52] U.S. Cl. .................................... 514/370; 548/161; 548/190; 548/193; 548/194; 548/198

[58] Field of Search ............... 548/190, 194, 193, 198, 548/161; 424/270

[56] References Cited

FOREIGN PATENT DOCUMENTS 2040580  4/1971  Fed. Rep. of Germany ...... 548/190
7325494  7/1973  Japan .................................. 548/190

Primary Examiner—Robert Gerstl
Attorney, Agent, or Firm—Wenderoth, Lind & Ponack

[57] ABSTRACT

New 2-(2-propynylamino)thiazole and 2-(3-iodo-2-propynylamino)thiazole derivatives having anti-microbial activity which are used as an active ingredient in anti-microbial compositions for medical and agricultural use.

24 Claims, No Drawings

PROPYNYLAMINOTHIAZOLE DERIVATIVES

BACKGROUND OF THE INVENTION

This invention relates to (2-propynylamino)thiazole and (3-iodo-2-propynylamino)thiazole derivatives which have anti-microbial activity.

In the prior art, 2-(3-halo-2-propynylthio)benzothiazoles have been known to have anti-fungal activity (Jap. Pat. Pub. (Kokoku) No. 26938/1971). There has also been known that 3-(3-iodo-2-propynyloxy)benzothiazole compounds have the same activity (Jap. Pat. Pub. (Kokai) No. 79862/1978). Besides, 3-(3-iodo-2-propynyloxy)-5-methylisoxazole has been disclosed to be an anti-fungal and anti-septic agent for woods in Jap. Pat. Pub. (Kokai) No. 22365/1979. Meanwhile, (2-propynylamino)thiazoles and (3-iodo-2-propynylamino)thiazoles have neither been disclosed nor known as anti-microbial agents.

SUMMARY OF THE INVENTION

An object of the present invention is to provide new (2-propynylamino)thiazole derivatives and (3-iodo-2-propynylamino)thiazole derivatives of the formula I:

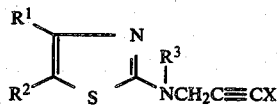

wherein
$R^1$ is hydrogen, $C_{1-4}$ alkyl, carboxy, formyl, hydroxy-$C_{1-4}$ alkyl, mono- or di-$C_{1-4}$ alkyl-aminomethyl, $C_{1-4}$ alkoxy-carbonyl, hydroxyiminomethyl, phenyl or

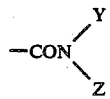

wherein Y is hydrogen or $C_{1-4}$ alkyl and Z is hydrogen, $C_{1-4}$ alkyl, $C_{1-4}$ alkoxy, hydroxy-$C_{1-4}$ alkyl or carboxy-$C_{1-4}$ alkyl;
$R^2$ is hydrogen, $C_{1-4}$ alkyl, $C_{1-4}$ alkoxy-carbonyl or halogen; or
$R^1$ and $R^2$ when taken together with the attached carbons are a condensed benzene ring optionally substituted by 1 or 2 groups selected from the group consisting of $C_{1-4}$ alkyl and $C_{1-4}$ alkoxy;
$R^3$ is hydrogen or $C_{1-4}$ alkyl; and
X is hydrogen or iodine.

A further object of this invention is to provide an anti-microbial composition containing the above derivative, which is applied for medical use and agricultural use. Another object of the invention is to provide methods for protecting and treating human beings and agricultural and horticultural products with the antimicrobial compositions.

DETAILED DESCRIPTION OF THE INVENTION

This invention relates to novel (2-propynylamino)-thiazole derivatives, more particularly thiazole derivatives substituted by 2-propynylamino or 3-iodo-2-propynylamino at the 2 position.

In these days, many penicillins and cephalosporins have been studied and developed and a number of drugs against both gram-positive and gram-negative bacteria have come into the market. On the other hand, there has been a noticeable increase in hardly remediable dermatomycosis and mycosis of the internal organs caused by profunda fungi.

The fungicide on the market for combatting these diseases has restricted application because of its side-effect. Accordingly, there is still a need for development of a new fungicide without any adverse side-effect. The desired compound of this invention satisfies this requirement.

The desired compound of this invention is represented by the formula I noted above.

In the definition, "$C_{1-4}$ alkyl" includes straight-chain and branched alkyls containing 1 to 4 carbon atoms such as methyl, ethyl, propyl, isopropyl, butyl and t-butyl.

"$C_{1-4}$ alkoxy" includes straight-chain and branched alkoxy such as methoxy, ethoxy, propoxy, isopropoxy and butoxy.

The terms, alkyl and alkoxy used in "hydroxy-$C_{1-4}$ alkyl", "mono- or di-$C_{1-4}$ alkyl-aminomethyl", "$C_{1-4}$ alkoxy-carbonyl", "carboxy-$C_{1-4}$ alkyl" and

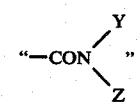

each includes the above definition of "$C_{1-4}$ alkyl" and "$C_{1-4}$ alkoxy".

The invention includes the salts of Compound I, for example, acid addition salts and metal salts. As the acid-addition salts, there are exemplified hydrochloride, hydrobromide, hydroiodide, nitrate, sulfate, phosphate, methanesulfate, acetate, citrate, maleate, malate, succinate, phthalate, cinnamate, benzoate, ascorbate and the like. Examples of the metal salt are a salt with an alkali metal (e.g. sodium or potassium), an alkaline earth metal (e.g. calcium or barium) and the like.

Preferred $R^1$ is hydrogen, $C_{1-4}$ alkyl and phenyl, specifically hydrogen, methyl and phenyl, more specifically hydrogen and methyl. Preferred $R^2$ is hydrogen, $C_{1-4}$ alkyl and halogen, specifically, hydrogen, methyl, ethyl, propyl and chlorine, more specifically hydrogen, methyl, ethyl and propyl.

Furthermore, $R^1$ and $R^2$ when taken together with the attached carbons may form a condensed benzene ring optionally substituted by 1 or 2 groups selected from the group consisting of $C_{1-4}$ alkyl and $C_{1-4}$ alkoxy; for example, benzene or $C_{1-4}$ alkyl-, di-$C_{1-4}$ alkyl-, $C_{1-4}$ alkoxy-, di-$C_{1-4}$ alkoxy- or $C_{1-4}$ alkyl-$C_{1-4}$ alkoxybenzene, more specifically, benzene, methylbenzene, dimethylbenzene, methoxybenzene or dimethoxybenzene, most specifically benzene, 6-methylbenzene or 4,5-dimethyl benzene with the numbering as follows:

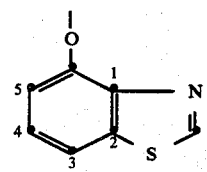

Preferred $R^3$ is hydrogen, methyl, ethyl and propyl; specifically hydrogen and methyl.

Compound I in which X is iodine has stronger antimicrobial activity than Compound I in which X is hydrogen. Accordingly, the latter Compound I is preferably used as a starting compound to produce the former.

Typical examples of Compound I are as follows:

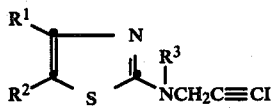

Ib

Compounds of the above formula Ib wherein
(1) $R^1$, $R^2$ and $R^3$ each is hydrogen,
(2) $R^1$ and $R^2$ each is hydrogen and $R^3$ is methyl,
(3) $R^1$ and $R^2$ each is hydrogen and $R^3$ is propyl,
(4) $R^1$ and $R^3$ each is hydrogen and $R^2$ is methyl,
(5) $R^1$ is hydrogen, $R^2$ and $R^3$ each is methyl,
(6) $R^1$ and $R^3$ each is hydrogen and $R^2$ is ethyl,
(7) $R^1$ is hydrogen, $R^2$ is ethyl and $R^3$ is methyl,
(8) $R^1$ and $R^3$ each is hydrogen and $R^2$ is propyl,
(9) $R^1$ is hydrogen, $R^2$ is propyl and $R^3$ is methyl,
(10) $R^1$ is hydrogen, $R^2$ is methoxycarbonyl and $R^3$ is methyl,
(11) $R^1$ and $R^3$ each is hydrogen and $R^2$ is ethoxycarbonyl,
(12) $R^1$ and $R^3$ each is hydrogen and $R^2$ is t-butoxycarbonyl,
(13) $R^1$ and $R^3$ each is hydrogen and $R^2$ is iodine,
(14) $R^1$ is hydrogen, $R^2$ is chlorine and $R^3$ is methyl,
(15) $R^1$ is methyl and $R^2$ and $R^3$ each is hydrogen,
(16) $R^1$ and $R^3$ each is methyl and $R^2$ is hydrogen,
(17) $R^1$ is methyl, $R^2$ is hydrogen and $R^3$ is ethyl,
(18) $R^1$ is methyl, $R^2$ is hydrogen and $R^3$ is propyl,
(19) $R^1$, $R^2$ and $R^3$ each is methyl,
(20) $R^1$ and $R^2$ each is methyl and $R^3$ is hydrogen,
(21) $R^1$ and $R^3$ each is methyl and $R^2$ is ethoxycarbonyl,
(22) $R^1$ is methyl, $R^2$ is butoxycarbonyl and $R^3$ is butyl,
(23) $R^1$ is methyl, $R^2$ is chlorine and $R^3$ is hydrogen,
(24) $R^1$ is propyl and $R^2$ and $R^3$ each is hydrogen,
(25) $R^1$ is propyl, $R^2$ is hydrogen and $R^3$ is methyl,
(26) $R^1$ and $R^2$ each is propyl and $R^3$ is hydrogen,
(27) $R^1$ is propyl, $R^2$ is methoxycarbonyl and $R^3$ is methyl,
(28) $R^1$ is propyl, $R^2$ is chlorine and $R^3$ is hydrogen,
(29) $R^1$ is butyl and $R^2$ and $R^3$ each is hydrogen,
(30) $R^1$ is butyl, $R^2$ is hydrogen and $R^3$ is methyl,
(31) $R^1$ is i-butyl, $R^2$ is chlorine and $R^3$ is methyl,
(32) $R^1$ is t-butyl, $R^2$ is bromine and $R^3$ is methyl,
(33) $R^1$ is carboxy, $R^2$ is hydrogen and $R^3$ is methyl,
(34) $R^1$ is carboxy, $R^2$ is methoxycarbonyl and $R^3$ is hydrogen,
(35) $R_1$ is formyl, $R_2$ is hydrogen and $R^3$ is methyl,
(36) $R^1$ is formyl, $R^2$ is ethoxycarbonyl and $R^3$ is ethyl,
(37) $R^1$ is hydroxymethyl, $R^2$ is hydrogen and $R^3$ is methyl,
(38) $R^1$ is methylaminomethyl and $R^2$ and $R^3$ each is hydrogen,
(39) $R^1$ is methylaminomethyl, $R^2$ is methoxycarbonyl and $R^3$ is methyl,
(40) $R^1$ is propylaminomethyl, $R^2$ is hydrogen and $R^3$ is methyl,
(41) $R^1$ is dimethylaminomethyl, $R^2$ is hydrogen and $R^3$ is methyl,
(42) $R^1$ is diethylaminomethyl and $R^2$ and $R^3$ each is hydrogen,
(43) $R^1$ is methoxycarbonyl, $R^2$ is hydrogen and $R^3$ is methyl,
(44) $R^1$ is ethoxycarbonyl and $R^2$ and $R^3$ each is ethyl,
(45) $R^1$ is butoxycarbonyl, $R^2$ is chlorine and $R^3$ is hydrogen,
(46) $R^1$ is hydroxyiminomethyl, $R^2$ is hydrogen and $R^3$ is methyl,
(47) $R^1$ is hydroxyiminomethyl, $R^2$ is chlorine and $R^3$ is methyl,
(48) $R^1$ is phenyl, $R^2$ is hydrogen and $R^3$ is methyl,
(49) $R^1$ is phenyl, $R^2$ is hydrogen and $R^3$ is propyl,
(50) $R^1$ is phenyl, $R^2$ is chlorine and $R^3$ is methyl,
(51) $R^1$ is methylaminocarbonyl and $R^2$ and $R^3$ each is hydrogen,
(52) $R^1$ is ethylaminocarbonyl and $R^2$ and $R^3$ each is hydrogen,
(53) $R^1$ is methoxyaminocarbonyl, $R^2$ is hydrogen and $R^3$ is methyl,
(54) $R^1$ is hydroxymethylaminocarbonyl, $R^2$ is methoxycarbonyl and $R^3$ is hydrogen,
(55) $R^1$ is carboxymethylaminocarbonyl, $R^2$ is hydrogen and $R^3$ is methyl,
(56) $R^1$ is dimethylaminocarbonyl, $R^2$ is hydrogen and $R^3$ is methyl,
(57) $R^1$ is diethylaminocarbonyl and $R^2$ and $R^3$ each is hydrogen,
(58) $R^1$ is diethoxyaminocarbonyl, $R^2$ is hydrogen and $R^3$ is methyl and
(59) $R^1$ is N-methyl-N-hydroxyethylaminocarbonyl, $R^2$ is hydrogen and $R^3$ is methyl, and Compound I of which $R^1$ and $R^2$ are linked:
(60) 2-(3-iodo-2-propynylamino)benzothiazole,
(61) 2-(N-methyl-3-iodo-2-propynylamino)benzothiazole,
(62) 2-(N-ethyl-3-iodo-2-propynylamino)benzothiazole,
(63) 2-(3-iodo-2-propynylamino)-4-methylbenzothiazole,
(64) 2-(N-methyl-3-iodo-2-propynylamino)-4-methylbenzothiazole,
(65) 2-(3-iodo-2-propynylamino)-6-methylbenzothiazole,
(66) 2-(N-ethyl-3-iodo-2-propynylamino)-6-methylbenzothiazole,
(67) 2-(3-iodo-2-propynylamino)-5,6-dimethylbenzothiazole,
(68) 2-(N-methyl-3-iodo-2-propynylamino)-5,6-dimethylbenzothiazole,
(69) 2-(3-iodo-2-propynylamino)-5-ethylbenzothiazole,
(70) 2-(N-methyl-3-iodo-2-propynylamino)-6-propylbenzothiazole,
(71) 2-(N-methyl-3-iodo-2-propynylamino)-6-methoxybenzothiazole,
(72) 2-(3-iodo-2-propynylamino)-6-ethoxybenzothiazole,
(73) 2-(3-iodo-2-propynylamino)-5,6-dimethoxybenzothiazole,
(74) 2-(N-methyl-3-iodo-2-propynylamino)-5,6-dimethoxybenzothiazole, and the corresponding Compound I of which X is hydrogen.

The desired Compound I can be prepared through various routes, one of which is illustrated as follows:

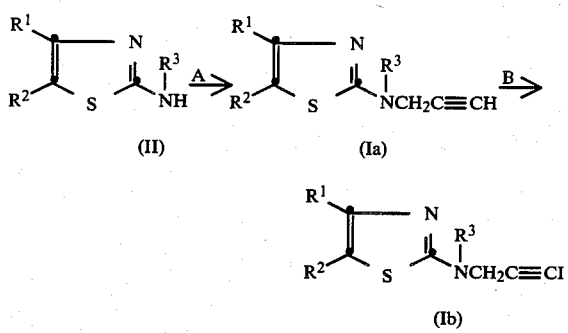

wherein $R^1$, $R^2$ and $R^3$ each has the same meaning as noted above.

The starting compound, 2-aminothiazole derivative (II) is reacted with 2-propynyl halide and the resultant 2-(2-propynylamino)thiazole derivative (Ia) is subjected to iodination to give 2-(3-iodo-2-propynylamino)-thiazole derivative (Ib) according to the above route. The substituents at the positions 4 and 5 may be protected, deprotected or modified in the course of the above process if they have liable functional groups. Step A (1) and Step B (2) and modification of the substituents at the positions 4 and 5 (3) are described below.

(1) Step A: Introduction of 2-propynyl group

2-Propynyl group is introduced into Compound II on reaction with 2-propynyl halide or di-(2-propynyl)sulfate. The reaction of Compound II with 2-propynyl halide (e.g. 2-propynyl bromide or 2-propynyl iodide) is effected in an inert solvent (e.g. ethers, benzenes, halogenohydrocarbons, esters or amides) under cooling, at room temperature or with heating in the presence of a base (e.g. sodium hydride, butyllithium, potassium hydroxide or sodium hydroxide). Tetrahydrofuran and dimethylformamide are preferred and tetrahydrofuran is more preferable. The reaction with di-(2-propynyl)sulfate is effected in a mixture of an aqueous solution of an alkali metal hydroxide (e.g. potassium hydroxide or sodium hydroxide) and an inert solvent (e.g. methylene chloride, chloroform, or benzene) in the presence of a generally employed phase-transfer reagent (e.g. benzyl triethyl ammonium chloride or tetrabutyl ammonium chloride) usually at room temperature or, if necessary, under cooling or heating.

The amino group at the position 2 of the thiazole ring should be changed to mono-substituted amino with a suitable amino-protecting group, if Compound II of which $R^3$ is hydrogen is applied as a starting compound. The amino-protecting group is removed after introduction of the 2-propynyl group in the usual manner.

The modification with an amino-protecting group is practised in the usual manner; for example, with an acyl halide (e.g. acetyl chloride or ethoxycarbonyl chloride) or an alkoxyalkyl halide (e.g. methoxymethyl chloride) in the presence of a base (e.g. pyridine) in an inert solvent (e.g. ethers, benzenes, halogenohydrocarbons or esters) at a room temperature or under heating. Removal of the amino-protecting group is effected with an acid (e.g. hydrochloric acid) or an alkali (e.g. sodium hydroxide or potassium hydroxide) in the usual manner.

(2) Step B: Iodination of Compound Ia

Iodination of Compound Ia is effected in the usual manner. It is practised with iodine and an alkali metal compound (e.g. butyllithium, potassium hydroxide, sodium hydroxide or potassium carbonate) in an inert solvent at room temperature or under cooling. The reaction proceeds smoothly in an ether such as tetrahydrofuran, ether and the like when alkyllithium is used as a base or in an aqueous or an anhydrous alcohol when an alkali metal hydroxide is employed.

(3) Modification of substituents

The desired Compound Ia or Ib having a substituent or substituents at the position 4 and/or 5 of the thiazole ring can be prepared by subjecting Compound II having the corresponding substituent to the reactions in Steps A and B. In this reaction, when the desired substituent is liable to the reaction condition of Steps A and/or B, it may be protected or modified, wherein reactivity of the intermediate and influence to the yield are also taken into account.

The modification of the substituent including protection and deprotection is practised by the usual method. Some examples are illustrated below.

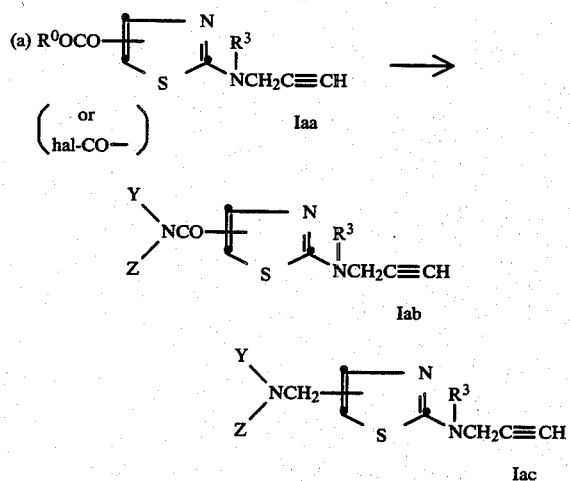

wherein $R^0$ is $C_{1-4}$ alkyl, hal is halogen and $R^3$, Y and Z each has the same meaning as noted above.

The substituted aminocarbonyl group which is illustrated as

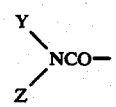

in Compound Iab is formed by reacting an alkoxycarbonyl $R^0OCO$ or the reactivated group, halogenocarbonyl hal—CO— with an amine,

The reaction is practised in an alcohol at room temperature or under heating.

The alkylaminomethyl or dialkylaminomethyl group which is illustrated as

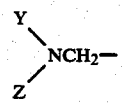

in Compound Iac is formed by reducing the corresponding amide,

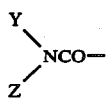

in Compound Iab with an alkali metal hydride (e.g. lithium aluminium hydride) in an ether (e.g. tetrahydrofuran).

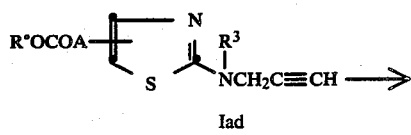

wherein A is $C_{1-4}$ alkylene and $R^0$ and $R^3$ each has the same meaning as noted above.

The hydroxyalkyl group being illustrated as HOCH$_2$—A— in Compound Iae is formed by reducing the corresponding carboxylic acid ester $R^0$OCOA—. The reduction is effected in the same manner as noted in the above (a).

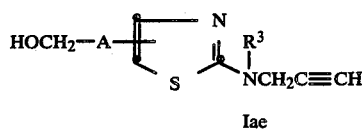

wherein $R^3$ has the same meaning as noted above. The formyl group in the position 4 or 5 of Compound Iag is formed by oxidizing hydroxymethyl. Oxidation is effected in the usual manner; i.e. with manganese dioxide or chromium trioxide.

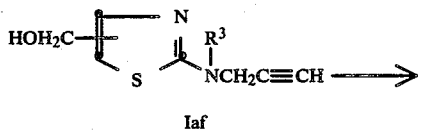

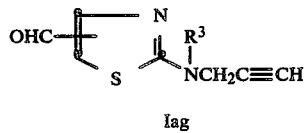

wherein $R^3$ has the same meaning as noted above. The hydroxyiminomethyl group on Compound Ibb is formed by reacting a formyl group with hydroxylamine in an alcohol.

The above procedures are well known in the synthetic field and can be employed depending on the desired compound.

Both Compounds Ia and Ib as well as their salts have anti-microbial activity. Compound Ib, however, is much superior to Compound Ia in the activity. Therefore, Compound Ia is preferably used to produce Compound Ib as noted above.

Some test results of Compound I are shown below with respect to the anti-fungal activity against pathogenic fungi of human beings and domestic animals as well as agricultural and horticultural fungi.

Test A-1 Anti-fungal Activity (MIC)

The following results (Table A) were obtained in an anti-fungal activity test in vitro against *Candida albicans* M-9, *Aspergillus fumigatus* and *Trichophyton asteroides*. The concentration of the test cells was $1 \times 10^5$ cells/ml and the activity was determined by a microwell dilution method. The number of the test compounds corresponds to that of the iodo compounds in the Examples.

Test A-2 Anti-fungal Activity (MCC)

Some MCC (Minimal Cidal Concentration) values (Table A) were obtained against *Candida albicans* and *Trichophyton asteroides* by the following method. After MIC value was obtained by the microwell method, a loopful amount was picked up from the medium in which no visible growth of the fungus was observed, reinoculated onto a Subouraud's glucose agar medium and incubated at 28° C. for 2 days in the case of *C. albicans* and for 7 days in the case of *T. asteroides*. The minimal concentration at which the fungi did not grow was recognized as MCC value.

TABLE A

| | MIC (γ/ml) | | | MCC (γ/ml) | |
|---|---|---|---|---|---|
| Comp. No. | Candida albicans M-9 | Aspergillus fumigatus | Trichophyton asteroides | Candida albicans M-9 | Trichophyton asteroides |
| 1 | 1.6 | 1.6 | 0.8 | | |
| 2 | <0.1 | 1.6 | 1.6 | 3.1 | 0.4 |
| 3 | 0.4 | 0.8 | 0.8 | 12.5 | 0.8 |
| 4 | 0.8 | 1.6 | 1.6 | | |
| 5 | 0.4 | 0.4 | 0.2 | 25 | 1.6 |
| 6 | 3.1 | 3.1 | 1.6 | | |
| 7 | 0.8 | 1.6 | 0.8 | 50 | 3.1 |
| 8 | 3.1 | 3.1 | 1.6 | | |
| 9 | 6.2 | 6.2 | 3.1 | | |
| 10 | 1.6 | 1.6 | 0.4 | | |
| 11 | 12.5 | >100 | 6.3 | | |
| 12 | 50 | >100 | 3.1 | | |
| 13 | >100 | >100 | 3.1 | | |
| 14 | 0.8 | 3.1 | 1.6 | | |
| 15 | 25 | 100 | >100 | | |
| 16 | 50 | >100 | 1.6 | | |

TABLE A-continued

| Comp. No. | MIC (γ/ml) Candida albicans M-9 | Aspergillus fumigatus | Trichophyton asteroides | MCC (γ/ml) Candida albicans M-9 | Trichophyton asteroides |
| --- | --- | --- | --- | --- | --- |
| 17 | 25 | 25 | 1.6 | | |
| 18 | 0.8 | 6.3 | 3.1 | | |
| 19 | 6.3 | 12.5 | 0.4 | | |
| 20 | 3.1 | 3.1 | 1.6 | | |
| 21 | 0.4 | 0.8 | 1.6 | | |
| 22 | 0.4 | 0.4 | 0.8 | | |
| 23 | 3.1 | 6.2 | 1.6 | | |
| 24 | 100 | 100 | 6.3 | | |
| 25 | >100 | >100 | 12.5 | | |
| 26 | 50 | 100 | 12.5 | | |
| 27 | >100 | >100 | >100 | | |
| 28 | 3.1 | 6.3 | 1.6 | | |
| Clotrimazole | 6.3 | 12.5 | 0.2 | >100 | 63 |

Notes:
1 Comp. Nos. 5, 7, 8, 9, and 10 are hydrochloride. Comp. No. 15 is sodium salt.

2 Clotrimazole: 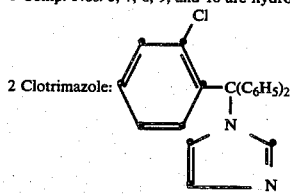

Test B-1 Control Test of Botrytis Rot (Gray Mold) of Cucumber

Seedlings of cucumber (Cultivar: Matsukaze) were planted and grown in soil in vinyl-chloride cups of 9 cm in diameter in a greenhouse. At the primary leaf stage, 2.5 ml each of a solution containing a prescribed concentration of a test compound was applied over the above cucumbers having been kept at 25°–26° C. for 1 day. Five pieces of absorbent cotton of 6 mm in diameter were put on a primary leaf and a spore suspension of *Botrytis cinerea* was inoculated dropwise onto the cotton. The treated cucumbers were kept for 3 days in a greenhouse (20° C.) and then the degree of infection was observed.

Standard of Evaluation (1) No disease; x 0
(2) A slight soaked lesion on the reverse of the test leaf; x 5
(3) A slight fade on the reverse of the leaf; x 10
(4) The inoculated part was faded and the fading expanded erosively; x 20

Disease Degree =

$$\frac{20 \times (4) + 10 \times (3) + 5 \times (2) + 0 \times (1)}{20 \times \text{Cotton piece Number}} \times 100$$

Percent Disease Control (%) =

$$\frac{\left(\begin{array}{c}\text{Disease Degree in}\\\text{Untreated Plot}\end{array}\right) - \left(\begin{array}{c}\text{Disease Degree in}\\\text{Treated Plot}\end{array}\right)}{\text{Disease Degree in Untreated Plot}} \times 100$$

TABLE B-1

| Comp.No. | Concentration (ppm) | Percent Disease Control (%) |
| --- | --- | --- |
| 1 | 500 | 100 |
| 5 | 500 | 100 |
| 6 | 500 | 100 |
| Untreated | — | 0 |

Test B-2 Control Test to Sclerotinia Rot of Cucumber

Cucumber seedlings were sprayed with 2.5 ml of a test solution in the same manner as in Test B-1. After the spraying, the seedlings were kept at 25°–26° C. for a day and three disks of 4 mm in diameter containing mycelia of *Sclerotinia sclerotiorum* were put on a primary leaf and then 10 μl of PD broth were dropped on the disks. The treated seedlings were kept in a greenhouse (20° C.) for 2 days and then the diameters of the disease spots were measured by a pair of slide calipers.

PD broth = potato-Dextrose broth

Percent Disease Control (%) =

$$\frac{\left(\begin{array}{c}\text{Diameter of Disease}\\\text{Spots of Untreated Plot}\end{array}\right) - \left(\begin{array}{c}\text{Diameter of Disease}\\\text{Spots of Treated Plot}\end{array}\right)}{\text{Diameter of Disease Spots of Untreated Plot}} \times 100$$

TABLE B-2

| Comp. No. | Concentration (ppm) | Percent Disease Control (%) |
| --- | --- | --- |
| 1 | 500 | 100 |
| 2 | 500 | 100 |
| 5 | 500 | 100 |
| 6 | 500 | 100 |
| 7 | 500 | 100 |
| 17 | 500 | 83 |
| Untreated | — | 0 |

Test B-3 Control Test to Downy Mildew of Cucumber

Each cucumber seedling was sprayed with 2.5 ml of a test solution in the same manner as in Test B-1. After the spraying, the seedlings were kept at 25°–26° C. for a day and a zoosporangium suspension of *Pseudoperonospora cubensis* was inoculated at a ratio of five spots per leaf on a primary leaf. The treated seedlings were kept in a greenhouse for 7 days and then observed.

Standard of Evaluation (1) No disease; x 0
(2) Slight disease at the inoculation spot; x 5
(3) A disease spot in the same size as the inoculation spot (without spreading); x 10
(4) A disease spot larger than the inoculation spot; x 20

Percent disease control were calculated in the same manner as in Test B-1.

TABLE B-3

| Result Comp. No. | Concentration (ppm) | Percent Disease Control (%) |
|---|---|---|
| 2 | 500 | 100 |
| 3 | 500 | 100 |
| 5 | 500 | 90 |
| 13 | 500 | 100 |
| 16 | 500 | 100 |
| 17 | 500 | 100 |
| Untreated | — | 0 |

Test B-4 Control Test to Anthracnose of Cucumber

Each cucumber seedling was sprayed with 2.5 ml of a test solution in the same manner as in Test B-1. After the spraying, the seedlings were kept at 25°–26° C. for a day and were inoculated with five filter-paper disks of 6 mm in diameter saturated with a conidium suspension of *Colletotrichum lagenarium* at a concentration of $1 \times 10^6$ conidia/ml. The treated seedlings were kept in a greenhouse (25° C.) for 3 days and further kept at below 25° C. for 3 days.

Standard of Evaluation

The same as noted in Test B-3.

TABLE B-4

| Result Comp. No. | Concentration (ppm) | Percent Disease Control (%) |
|---|---|---|
| 1 | 500 | 100 |
| 2 | 500 | 100 |
| 3 | 500 | 100 |
| 7 | 500 | 100 |
| 13 | 500 | 100 |
| 16 | 500 | 100 |
| 17 | 500 | 100 |
| Untreated | — | 0 |

Test B-5 Control Test to Powdery Mildew of Cucumber

Each cucumber seedling was sprayed with 2.5 ml of a test solution in the same manner as in Example B-1. The seedlings were kept at 25°–26° C. for 1 day after the spraying and then sprayed with a conidium suspension ($1 \times 10^5$ conidia/ml) of *Sphaerotheca fuliginea* in a 100 ppm spreader solution (containing 20% polyoxyethylene glycol alkyl phenol ether and 12% lignin sulfonate) at a ratio of 25 ml/20 cups.

The seedlings were kept in a greenhouse (25° C.) for 2 weeks and then observed.

Standard of Evaluation $$\text{Disease Degree} = \frac{\text{Diseased Area}}{\text{Leaf Area}} \times 100$$

The percent disease control was calculated in the same manner as in Test B-1.

TABLE B-5

| Result Comp. No. | Concentration (ppm) | Percent Disease Control (%) |
|---|---|---|
| 1 | 500 | 100 |
| 2 | 500 | 100 |
| 3 | 500 | 100 |
| 5 | 500 | 100 |
| 6 | 500 | 100 |
| 7 | 500 | 100 |
| 8 | 500 | 100 |
| 9 | 500 | 100 |
| 16 | 500 | 100 |
| 17 | 500 | 100 |
| 18 | 500 | 100 |
| Untreated | — | 0 |

All Compounds I in the above tests show anti-fungal activity against pathogenic fungi of human beings and agricultural products. Compounds I including those tested above and the others as well as the salts have anti-fungal and anti-bacterial activities and are usable as an anti-microbial agent in the fields of medicine agriculture, horticulture and forestry. Accordingly, Compound I is employed as an ingredient of anti-microbial compositions for medical and agricultural use. The term "agricultural" includes agricultural, horticultural and forestry hereinafter.

Compound I, when used as medicine, is mixed with and dissolved in pharmaceutically acceptable suitable adjuvants such as carriers, diluents, flavorings, aromatics and surfactants, and is formulated into tablets, capsules, powders and the like for oral administration and injection, ointment, suppositories and the like for parenteral aministration. The composition is prepared by mixing with a suitable adjuvant to contain an effective amount of Compound I.

The dosage to be administered is determined depending on the kind of the diseases, the age and body weight of the patient and the like. The amount is, for example, about 100 mg to about 500 mg per day for an adult patient when Compound I is administered orally. Compound I is formulated into an anti-microbial compostion for agricultural use comprising as an active ingredient about 0.01 to about 90 weight percent of Compound I based on the weight of the composition, by mixing with a suitable solid or liquid carrier and other suitable adjuvants such as surfactants, diluents, spreaders and synergists. Solid carriers include talc, clay, bentonite, pyrophyllite, kaolin, diatomaceous earth, silica and the like. Liquid carriers include water, methanol, ethanol, acetone, dimethyl formamide, ether, benzene, xylene, toluene, naphtha and the like. Surfactants include non-ionic surfactants (e.g. polyoxyethylene alkyl phenyl ethers or polyoxyethylene fatty acid esters), anionic surfactants (e.g. alkylbenzene sulfonic acid salts, lignin sulfonic acid salts or dinaphthylmethane sulfonic acid salts), polyvinyl alcohols, CMC, gum arabic and the like.

The anti-microbial composition is formulated into powders, wettable powders, granules, emulsions, suspensions, solutions and the like and used for sterilizing agricultural products, seedlings, seed and the like as well as soil. Compound I, for example, is homogeneously dissolved in a hydrocarbon or an alcohol with a suitable surfactant to give an emulsion or a solution. It is mixed with a mineral powder and with a suitable surfactant, crushed and homogenized to fine powder to give a wettable powder. The thus-prepared composition is diluted with water to a desired concentration and sprayed. Alternatively, it may be diluted with mineral powder, homogeneously crushed, blended and used as a dust. Finally, the composition is diluted to contain an effective amount of Compound I. Besides, the composition can be combined with other agrochemicals, e.g. insecticides, sterilizers, herbicides, plant-growth regulators, miticides and the like. It also can be mixed with nutrients.

The composition is usally used at a concentration of about 50 to about 1000 ppm of Compound I when sprayed on agricultural products.

Additionally, Compound I may be used as an active ingredient of sterilizers for painting, timber, paper, cloth and the like. For example, an effective amount of Compound I may be mixed in a paint for ships to prevent adherence of shellfish and algae. A sterilizer containing Compound I at an effective concentration may be sprayed on wall-paper and wall-cloth.

The following examples are included merely to aid in the understanding of the invention and variations may be made by one skilled in the art without departing from the spirit and scope of the invention.

EXAMPLE 1

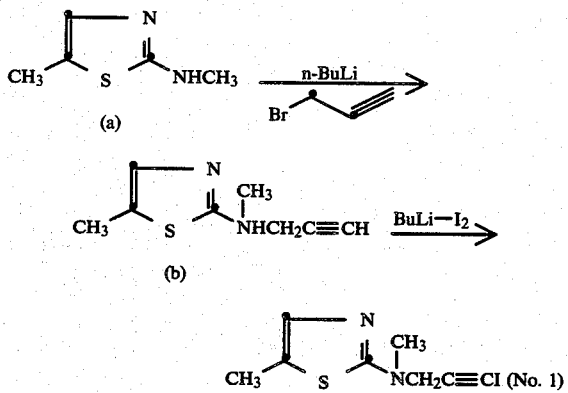

(1) 2-Methylamino-5-methylthiazole (a) (1.00 g) was dissolved in tetrahydrofuran (30 ml) and a hexane solution (6.7 ml) of butyllithium was added thereto at $-78°$ C. The mixture was stirred for 1 hour and 2-propynyl bromide (1.14 g) was added thereto. The mixture was allowed to react at room temperature for 16 hours and then evaporated to remove the tetrahydrofuran. After addition of water, the residue was extracted with ether. The extract was washed with water and evaporated to remove the solvent. The resultant residue was applied to column chromatography on silica gel (30 g) to give 2-(N-methyl-2-propynylamino)-5-methylthiazole (b) from chloroform eluate as an oil (950 mg, yield 73%).

NMR $\delta_{CDCl_3}$ (J=Hz) 2.25d(1)3H, 2.25 1H, 3.00s 3H, 4.18d(2)2H, 6.78q(1)1H.

(2) Compound (b) (950 mg) was dissolved in anhydrous tetrahydrofuran (30 ml) and a hexane solution (4.5 ml) of butyllithium was added thereto at $-78°$ C. After 30 minutes iodine (1.6 g) was added to the above mixture, which was then allowed to react for 10 minutes at room temperature and evaporated to remove the tetrahydrofuran. Water is added to the residue, which was then extracted with ether. The extract was washed with water and evaporated to remove the solvent. The residue was applied to chromatography on silica gel (25 g) to give 2-(N-methyl-3-iodo-2-propynylamino)-5-methylthiazole (No.1) (1.38 g, yield 83%) from chloroform eluate. mp. 97°–98° C. (hydrochloride: mp. 205°–213° C. (decomp.))

Elemental Analysis: Anal. Calcd. for $C_8H_9N_2SI$: C, 32.89; H, 3.11; N, 9.59; S, 10.98; I, 43.44, Found: C, 32.74; H, 3.20; N, 9.38; S, 11.20 (%).

EXAMPLE 2

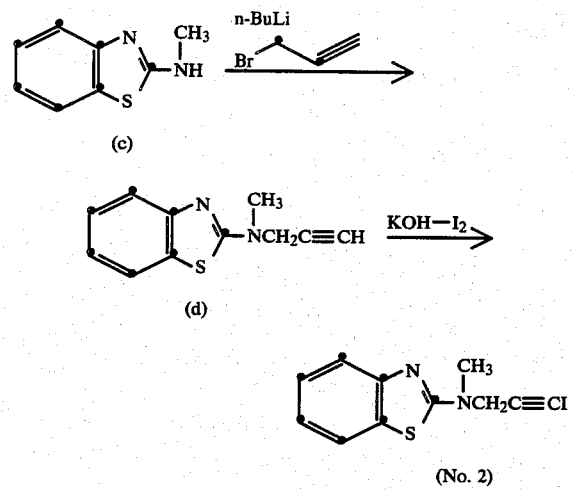

(1) 2-Methylaminobenzothiazole (c) (14.0 g) was dissolved in anhydrous tetrahydrofuran (250 ml) and a hexane solution (73 ml) of butyl lithium (6.53 g) was added thereto at $-78°$ C. with stirring. The mixture was stirred for 1.5 hours under cooling and 2-propynyl bromide (8.4 ml) was dropwise added thereto. The resultant mixture was allowed to stand at room temperature overnight and then evaporated to remove the solvent. After addition of water, the residue was extracted with ether. The extract was washed with water, dried and evaporated to remove the solvent. The resultant residue was applied to column chromatography on silica gel (280 g) to give 2-(N-methyl-N-propynylamino)benzothiazole (d) (14.5 g, yield 84%) from chloroform eluate.

mp. 58°–59° C. (ether-hexane).

Elemental analysis: Calcd. for $C_{11}H_{10}N_2S$: C, 65.32; H, 4.98; N, 13.85; S, 15.85, Found: C, 65.20; H, 4.86; N, 13.67; S, 16.03 (%).

(2) Compound (d) (2.02 g) was dissolved in a mixture of methanol (35 ml), water (10 ml) and 86% potassium hydroxide (1.4 g) and then iodine (2.66 g) was added in small portions with stirring under ice-cooling. The mixture was stirred at room temperature for 1.5 hours and then water was added thereto. The resultant crystals were filtered off, washed with water and dried to give 2-(N-methyl-3-iodo-2-propynylamino)benzothiazole (No.2) (3.27 g, yield 100%): mp. 100°–101° C. (decomp.) (acetone-hexane), Hydrochloride: mp. 156°–160° C. (decomp.), Nitrate: mp. 108°–109° C. (decomp.), Hydrobromide: mp. 158°–160° C. (decomp.).

Elemental Analysis: Anal. Calcd. for $C_{11}H_9N_2SI$: C, 40.26; H, 2.76; N, 8.54; S, 9.77; I, 38.67, Found: C, 40.51; H, 2.84; N, 8.37; S, 9.57; I, 38.53 (%).

EXAMPLE 3

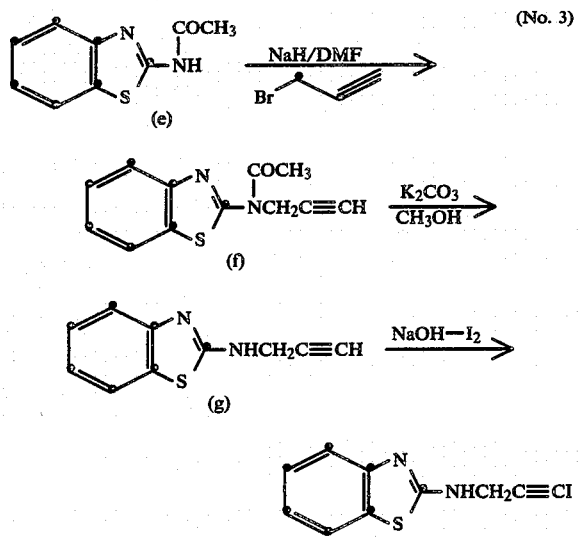

(1) 2-Acetylaminobenzothiazole (e) (6.0 g) was dissolved in dimethylformamide (50 ml) and 50% sodium hydride (1.648 g) was added thereto in small portions with stirring under ice-cooling. The mixture was heated at 50° C. for 1 hour, then cooled to room temperature and 2-propynyl bromide (3.0 ml) was added thereto. The mixture was heated at 60° C. for 4 hours and evaporated to remove the solvent. After addition of water, the residue was extracted with benzene. The extract was washed with water, and evaporated to remove the solvent. The residue was applied to column chromatography on silica gel (120 g) to give 2-(N-acetyl-N-propynylamino)benzothiazole (f) (4.43 g, yield 62%) from chloroform eluate:

mp. 138°–139° C. (ether-hexane).

(2) A mixture of compound (f) (1.0 g), 80% methanol (20 ml) and potassium carbonate (1.0 g) was refluxed by heating for 1 hour and evaporated to remove the solvent. The residue was extracted with chloroform. The extract was washed with water, dried, and evaporated to remove the solvent. The residue was applied to column chromatography on silica gel (20 g) to give 2-(2-propynylamino)benzothiazole (g) (829 mg, yield 100%) from chloroform eluate: mp. 134°–135° C. (acetone-hexane).

(3) Compound (g) (328 mg) was iodinated in the same manner as in Example 2(2) using sodium hydroxide instead of potassium hydroxide to give crystalline residue. Recrystallization from chloroform-methylene chloride gives 2-(3-iodo-2-propynylamino)benzothiazole (No. 3) (65 mg, yield 12%):

mp. 141°–142° C. (decomp.).

Elemental Analysis: Anal. Calcd. for $C_{10}H_7N_2SI$, C, 38.23; H, 2.25; N, 8.92; S, 10.21; I, 40.40, Found: C, 38.53; H, 2.51; N, 9.18; S, 10.49; I, 40.31 (%).

EXAMPLES 4–19

The same procedure as noted in Examples 1–3 gave the compounds noted in Table 1.

TABLE 1

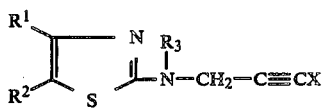

| Ex. No. | $R^1$ | $R^2$ | $R^3$ | Compound Ia (X = H) mp (°C.) or NMR $\delta^{CDCl_3}$ (J = Hz) | | Compound Ib (X = I) mp (°C.) | hydro- chloride mp (°C.) |
|---|---|---|---|---|---|---|---|
| 4 | H | H | CH$_3$ | oil | δ2.27 t (3), 3.07 s, 4.28 d (2), 6.52 d (3), 7.17 d (3) | 60–2 | |
| 5 | " | Et | " | " | δ1.23 t (7), 2.23 t (2), 2.67 q (7), 3.02 s, 4.20 d (2), 6.82 brs | oil | 130–2 |
| 6 | " | Pr | " | " | δ0.93 t (7), 1.55 m, 2.27 t (2), 2.63 t (2), 3.03 s, 4.22 d (2), 6.83 brs | 49–50 | 118–9 (d) |
| 7 | CH$_3$ | H | " | " | δ2.23 s, 2.25 t (2), 3.03 s, 4.27 d (2), 6.07 brs | oil | 143–4 (d) |
| 8 | " | " | Et | " | δ1.27 t (7), 2.23 t (2), 2.23 s, 3.53 q (7), 4.27 d (2), 6.07 brs | " | 136–7 (d) |
| 9 | " | " | Pr | " | δ0.93 t (7), 1.70 m, 2.22 s, 2.27 t (3), 3.40 t (7), 4.25 d (3), 6.02 brs | " | 146–8 (d) |
| 10 | " | CH$_3$ | CH$_3$ | " | δ2.13 s, 2.17 s, 2.23 t (2.5), 2.97 s, 4.17 d (2.5) | " | 151–3 (d) |
| 11 | " | EtOOC | " | mp. | 46° | 121–2 | |
| 12 | " | ⌬— | H | " | oil | δ2.18 t (2), 3.02 s, 4.26 d (2), 6.63 s | 86–7 | 142–4 (d) |
| 13 | " | Cl | " | " | δ2.23 t (3), 3.02 s, 4.23 d (3) | 85–6 (d) | |
| 14 | CH$_3$OOC— | H | " | mp. | 69–9.5° | 150–2 | |
| 15 | NaOOC— | " | " | " | | Sodium salt 200–210 (d) | |

TABLE 1-continued $$\begin{array}{c} R^1 \\ \diagdown \\ R^2 \end{array} \begin{array}{c} N \\ \diagup \\ S \end{array} \begin{array}{c} R_3 \\ | \\ N-CH_2-C\equiv CX \end{array}$$

| Ex. No. | $R^1$ | $R^2$ | $R^3$ | Compound Ia (X = H) mp (°C.) or NMR $\delta^{CDCl_3}$ (J = Hz) | Compound Ib (X = I) mp (°C.) | hydro-chloride mp (°C.) |
|---|---|---|---|---|---|---|
| 16 | —C=CH—CH=CH— <br> \| <br> CH$_3$ | | " | mp. 41–1.5° | 95–6 | 153–5 (d) |
| 17 | —CH=C——C=CH— <br> \|    \| <br> CH$_3$ CH$_3$ | | " | mp. 100–1° | 141–2 | 148–150 (d) |
| 18 | —CH=CH—C=CH— <br> \| <br> CH$_3$ | | " | mp. 42.5–4° | 97–7.5 | |
| 19 | —CH=CH—C=CH— <br> \| <br> OCH$_3$ | | " | mp. 62–4° | oil | Oxalate 136–8 (d) |

Note: Et = Ethyl, Pr = Propyl, d = decomp.

EXAMPLE 20

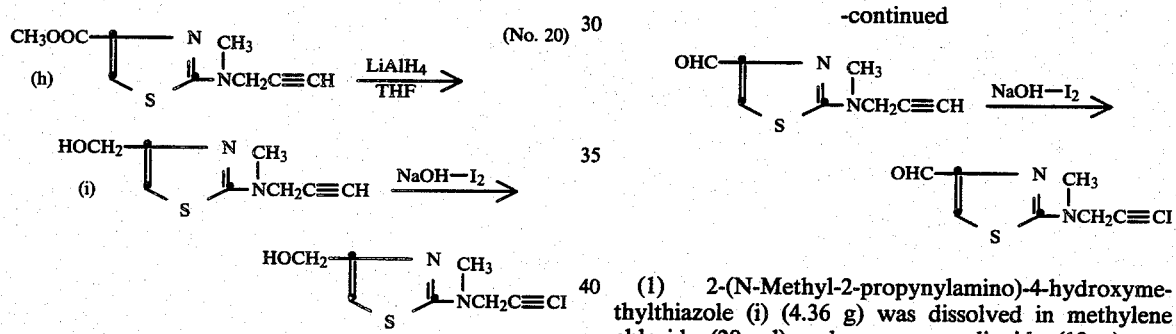

(1) Lithium aluminum hydride (900 mg) was added to anhydrous tetrahydrofuran (20 ml) and a solution of 2-(N-methyl-2-propynylamino)-4-methoxycarbonyl-thiazole (h) (5.0 g) in tetrahydrofuran (30 ml) was added dropwise thereto with stirring under ice-cooling. The mixture was refluxed for 2 hours, to which water was carefully added under ice-cooling, and evaporated to remove the tetrahydrofuran. The residue was extracted with chloroform. The extract was washed with water, dried and recrystallized from ether-hexane to give 2-(N-methyl-2-propynylamino)-4-hydroxymethylthiazole (i) (3.75 g, yield 86.5%): mp. 69°–70° C.

(2) Compound (i) was treated in the same manner as in Example 3(3) to give 2-(N-methyl-3-iodo-2-propynylamino)-4-hydroxymethylthiazole (No. 20): mp. 118°–119° C. (ether).

Elemental Analysis: Anal. Calcd. for C$_8$H$_9$N$_2$OSI, C, 31.18; H, 2.94; N, 9.09; S, 10.41; I, 41.18 Found: C, 31.52; H, 3.08; N, 9.29; S, 10.52; I, 40.96 (%).

EXAMPLE 21

(1) 2-(N-Methyl-2-propynylamino)-4-hydroxyme-thylthiazole (i) (4.36 g) was dissolved in methylene chloride (20 ml) and manganese dioxide (10 g) was added thereto. The mixture was stirred at room temperature for 16 hours and filtered off. The filtrate was evaporated and the residue was applied to column chromatography on silica gel (50 g) to give 2-(N-methyl-2-propynylamino)-4-formylthiazole (j) (2.56 g, yield 59%) from chloroform-ether (3:1) eluate as an oil.

IR: $\nu_{max}^{CHCl_3}$ 330, 1696 cm$^{-1}$.

NMR: $\delta_{CDCl_3}$ (J=Hz) 2.33t(2)1H, 3.17s3H, 4.37d(2)2H, 7.50s1H, 9.77s1H.

(2) Compound (j) was treated in the same manner as in Example 3(3) to give 2-(N-methyl-3-iodo-2-propynylamino)-4-formylthiazole (No. 21): mp. 141°–143° C. (decomp.)

IR: $\nu_{max}^{CHCl_3}$ 2175, 1692 cm$^{-1}$.

Elemental Analysis: Anal. Calcd. for C$_8$H$_7$N$_2$OSI: C, 31.39; H, 2.30; N, 9.15; S, 10.57; I, 41.45 Found: C, 31.61; H, 2.46; N, 9.29; S, 10.87; I, 41.03 (%).

EXAMPLE 22

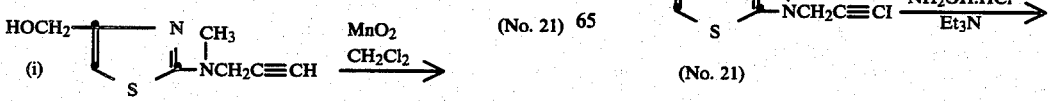

-continued

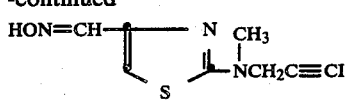

(No. 22)

To 2-(N-methyl-3-iodo-2-propynylamino)-4-formyl-thiazole (No. 21) (72 mg) were added methanol (5 ml), triethylamine (0.2 ml) and hydroxylamine hydrochloride (24 mg) and the mixture was stirred at room temperature for 4 hours and evaporated to remove the solvent. After addition of a 5% aqueous solution of potassium carbonate, the residue was extracted with chloroform. The extract was washed with water, dried and evaporated to remove the solvent. The crystalline residue was treated with acetone to give 2-(N-methyl-3-iodo-2-propynylamino)-4-hydroxyiminomethylthiazole (No. 22) melting at 155°–156° C. (decomp.).

Elemental Analysis: Anal. Calcd. for $C_8H_8N_3OSI$, C, 29.92; H, 2.51; N, 13.08; S, 9.98 Found: C, 30.27; H, 2.57; N, 13.36; S, 10.03 (%).

EXAMPLE 23

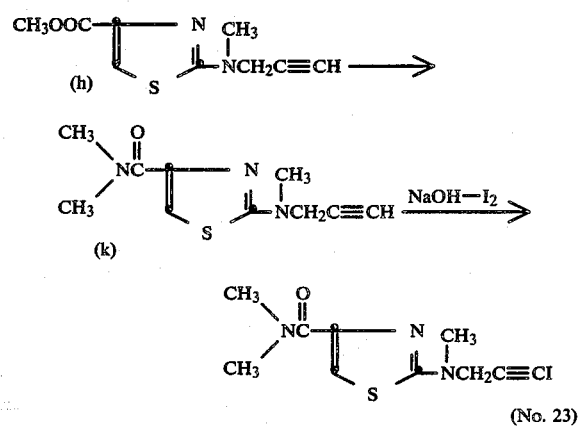

(No. 23)

(1) 2-(N-Methyl-2-propynylamino)-4-methoxycarbonylthiazole (h) (420 mg) with methanol (10 ml) and 1N sodium hydroxide (2.4 ml) was refluxed by heating for 30 minutes. The mixture was neutralized with 1N hydrochloric acid (2.4 ml), evaporated to remove the solvent and dried. After addition of methylene chloride (20 ml) and thionyl chloride (0.28 ml), the residue was refluxed for 1 hour and evaporated to remove the solvent. Methylene chloride (30 ml) was added to the residue and a 10% ethanol solution (4 ml) of diethylamine was added thereto at room temperature with stirring. The mixture was stirred for 30 minutes and evaporated to remove the solvent. The residue was extracted with chloroform. The extract was dried and evaporated to give crystalline residue. The residue was applied to column chromatography on silica gel (4 g) to give 2-(N-methyl-2-propynylamino)-4-dimethylaminocarbonyl-thiazole (k) (344 mg) from chloroform eluate:

mp. 99°–100° C. (ether)

IR: $\nu_{max}^{CHCl_3}$ 3300, 1620 cm$^{-1}$.

(2) Compound (k) was treated in the same manner as in Example 3(3) to give 2-(N-methyl-3-iodo-2-propynylamino)-4-dimethylaminocarbonylthiazole (No. 23). mp. 148°–150° C. (ether).

Elemental Analysis: Anal. Calcd. for $C_{10}H_{12}N_3OSI$: C, 34.40; H, 3.46; N, 12.03; S, 9.18; I, 36.34 Found: C, 34.73; H, 3.49; N, 11.87; S, 9.34; I, 36.28 (%).

EXAMPLE 24

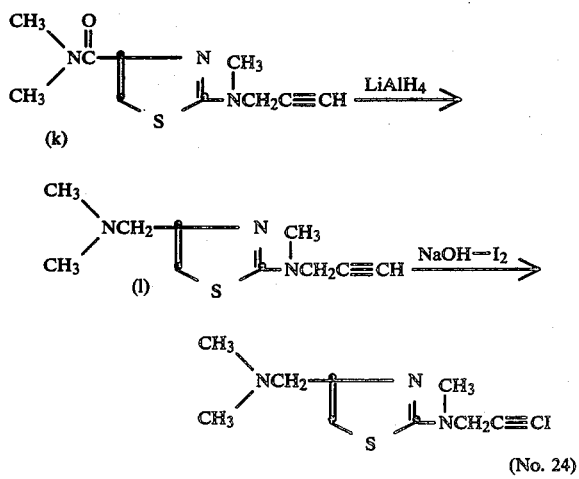

(No. 24)

2-(N-Methyl-2-propynylamino)-4-dimethylaminocarbonylthiazole (k) (474 mg) was dissolved in tetrahydrofuran (15 ml) and lithium aluminium hydride (250 mg) was added thereto at room temperature with stirring. The mixture was refluxed for 1 hour and, after decomposition of the excess lithium aluminium hydride with water, evaporated to remove the tetrahydrofuran. The residue was extracted with chloroform. The extract was washed with water, dried and evaporated to remove the solvent. The residue was applied to column chromatography on silica gel (10 g) to give 2-(N-methyl-2-propynylamino)-4-dimethylaminomethylthiazole (1) from chloroform-methanol (10:1) eluate as an oil (374 mg).

NMR: $\delta_{CDCl_3}$ (J=Hz) 2.27s6H, 2.27t(2)1H, 3.07s3H, 3.37s2H, 4.28d(2)2H, 6.33s1H. (2) Compound (1) was treated in the same manner as in Example 3(3) to give 2-(N-methyl-3-iodo-2-propynylamino)-4-dimethylaminomethylthiazole (No. 24). mp. 98°–100° C.

Elemental Analysis: Anal. Calcd. for $C_{10}H_{14}N_3SI$: C, 35.83; H, 4.21; N, 12.54; S, 9.57, Found: C, 35.61, H, 4.28; N, 12.75; S, 9.51 (%).

EXAMPLES 25–28

The same procedure as in Example 23 gave the following compounds.

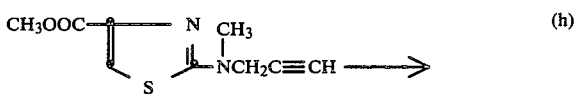

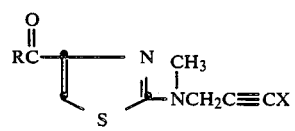

TABLE 2

| Ex. No. | R | X = H mp(°C.) or NMR $\delta^{CDCl_3}$(J = Hz) | X = I mp(°C.) |
|---|---|---|---|
| 25 | HOCH$_2$CH$_2$\N—/CH$_3$ | oil, δ2.37(2), 3.1s, 3.77m, 4.23(2), 4.67broad. 7.15s | 109–111 |
| 26 | HOOCCH$_2$NH— | (Ethyl ester) mp. 100–102 | 164–165(d) |
| 27 | HOCH$_2$CH$_2$NH— | oil, δ2.37t(2), 3.08s, 3.68m, 4.15br. 4.3d(s), 7.33s, 7.63br. | 158–159 |
| 28 | CH$_3$ONH— | δ2.33t(2), 3.07s, 3.83s 4.25d(2), 7.37s, 9.83s. | 154–155(d) |

EXAMPLE 29

Three parts (which means by weight ratio throughout the following examples) of Compound No. 5 (the iodide), 25 parts of white vaseline, 25 parts of stearyl alcohol, 12 parts of propylene glycol, 1.5 parts of sodium lauryl sulfate, 0.025 part of ethyl p-hydroxybenzoate, 0.015 part of propyl p-hydroxybenzoate and the balance of purified water (total 100 parts) are formulated to give an ointment.

EXAMPLE 30

A hundred parts of Compound No. 22, 50 parts of a mixture of hydroxypropyl starch, crystalline cellulose and aluminium silicate (60:20:20) are mixed and formulated to tablets.

EXAMPLE 31

Five parts of Compound No. 21 is dissolved in 100 parts of peanut oil to give an injectable solution.

EXAMPLE 32

Five parts of the hydrochloride of Compound No. 1, 20 parts of propylene alcohol, 5 parts of polyoxyethylene alkyl phenyl ether and 70 parts of water are mixed and dissolved to give a solution, which is diluted with water so that the effective concentration of Compound No. 1 is 50–500 ppm, and sprayed on leaves and stems.

EXAMPLE 33

Fifty parts of Compound No. 2, 6 parts of sodium alkyl benzenesulfonate, 4 parts of sodium ligninesulfonate and 40 parts of clay are mixed and crushed to give a wettable powder, which is diluted so that the effective concentration of Compound No. 2 is 50–500 ppm, and sprayed on fruit.

EXAMPLE 34

Five parts of Compound No. 5 (the iodide), 90 parts of an equivalent mixture of bentonite and talc and 5 parts of sodium alkylbenzene sulfonate are mixed crushed and formulated to granules.

EXAMPLE 35

Twenty-five parts of Compound No. 6 (the iodide), 8 parts of polyoxyethylene alkyl phenyl ether, 2 parts of sodium alkylbenzenesulfonate and 65 parts of xylene are mixed and dissolved to give a concentrated emulsion, which is diluted so that the effective concentration of Compound No. 6 is 50–500 ppm and sprayed on leaves and stems.

EXAMPLE 36

One part of Compound No. 13 (the iodide) was mixed with 99 parts of talc to give a dust.

EXAMPLE 37

A solution is prepared in the same manner as in Example 32 using Compound No. 17 (the iodide) instead of Compound No. 1.

EXAMPLE 38

An ointment is prepared in the same manner as in Example 29 using Compound No. 3 or Compound No. 17 (the iodide) instead of Compound No. 5.

While preferred embodiments of the invention have been described using specific terms, such description is for illustrative purposes only, and it is to be understood that changes and variations may be made without departing from the spirit and scope of the following claims.

What we claim is:

1. A compound selected from the group consisting of a compound of the formula I:

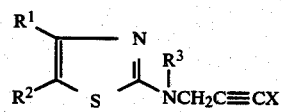

wherein

R$^1$ is hydrogen, C$_{1-4}$ alkyl, carboxy, formyl, hydroxy-C$_{1-4}$ alkyl, mono- or di-C$_{1-4}$ alkyl-aminomethyl, C$_{1-4}$ alkoxy-carbonyl, hydroxyiminomethyl, phenyl or

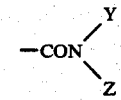

wherein Y is hydrogen or C$_{1-4}$ alkyl and Z is hydrogen, C$_{1-4}$ alkyl, C$_{1-4}$ alkoxy, hydroxy-C$_{1-4}$ alkyl or carboxy-C$_{1-4}$ alkyl;

R$^2$ is hydrogen, C$_{1-4}$ alkyl, C$_{1-4}$ alkoxy-carbonyl or halogen; or

R$^1$ and R$^2$ when taken together with the attached carbons are a condensed benzene ring optionally substituted by 1 or 2 groups selected from the group consisting of C$_{1-4}$ alkyl and C$_{1-4}$ alkoxy;

R$^3$ is hydrogen or C$_{1-4}$ alkyl; and

X is hydrogen or iodine, and a salt of said compound.

2. The compound claimed in claim 1 wherein R$^1$ is hydrogen, C$_{1-4}$ alkyl or phenyl.

3. The compound claimed in claim 1 wherein R$^1$ is hydrogen, methyl or phenyl.

4. The compound claimed in claim 1 wherein R$^2$ is hydrogen, C$_{1-4}$ alkyl or halogen.

5. The compound claimed in claim 1 wherein R$^2$ is hydrogen, methyl, ethyl, propyl or chlorine.

6. The compound claimed in claim 1 wherein R$^1$ and R$^2$ when taken together with the attached carbons form benzene, methylbenzene, dimethylbenzene, methoxybenzene, or dimethoxybenzene.

7. The compound claimed in claim 1 wherein R$^1$ and R$^2$ when taken together with the attached carbons form benzene, 6-methylbenzene or 4,5-dimethylbenzene.

8. The compound claimed in claim 1, wherein $R^3$ is hydrogen, methyl, ethyl or propyl.

9. The compound claimed in claim 1 wherein $R^3$ is hydrogen or methyl.

10. The compound claimed in claim 2 wherein $R^2$ is hydrogen, $C_{1-4}$ alkyl or halogen and $R^3$ is hydrogen, methyl, ethyl or propyl.

11. The compound claimed in claim 3 wherein $R^2$ is hydrogen, methyl, ethyl, propyl or chlorine and $R^3$ is hydrogen or methyl.

12. The compound claimed in claim 6 wherein $R^3$ is hydrogen, methyl, ethyl or propyl.

13. The compound claimed in claim 7 wherein $R^3$ is hydrogen or methyl.

14. The compound claimed in claim 1 which is 2-(N-methyl-3-iodo-2-propynylamino)-5-methylthiazole.

15. The compound claimed in claim 1 which is 2-(N-methyl-3-iodo-2-propynylamino)benzothiazole.

16. The compound claimed in claim 1 which is 2-(3-iodo-2-propynylamino)benzothiazole.

17. The compound claimed in claim 1 which is 2-(N-methyl-3-iodo-2-propynylamino)-5-ethylthiazole.

18. The compound claimed in claim 1 which is 2-(N-methyl-3-iodo-2-propynylamino)-5-propylthiazole.

19. The compound claimed in claim 1 which is 2-(N-methyl-3-iodo-2-propynylamino)-4-methylthiazole.

20. The compound claimed in claim 1 which is 2-(N-methyl-3-iodo-2-propynylamino)-4-methylbenzothiazole.

21. The compound claimed in claim 1 which is 2-(N-methyl-3-iodo-2-propynylamino)-5,6-dimethylbenzothiazole.

22. An anti-microbial composition for medical use which comprises an effective amount of the compound claimed in claim 1 as an active ingredient, and a suitable adjuvant.

23. An anti-microbial composition for agricultural use which comprises an effective amount of the compound claimed in claim 1 as an active ingredient 1 and a suitable adjuvant.

24. The composition claimed in claim 23 which contains about 0.01 to about 90 weight percent of the active ingredient.

* * * * *